United States Patent
Naidyhorski

[11] Patent Number: 6,102,044
[45] Date of Patent: Aug. 15, 2000

[54] ELECTRODE CARRYING SURGICAL DRAPE AND METHOD

[75] Inventor: Roger A. Naidyhorski, Stillwater, Minn.

[73] Assignee: Medical Concepts Development, Inc., Woodbury, Minn.

[21] Appl. No.: 09/415,584

[22] Filed: Oct. 8, 1999

[51] Int. Cl.⁷ ................................................... A61B 19/00
[52] U.S. Cl. ........................................ 128/849; 128/853
[58] Field of Search ................................ 128/849–856

[56] References Cited

U.S. PATENT DOCUMENTS

| | | | |
|---|---|---|---|
| 4,715,366 | 12/1987 | Teeple | 128/849 |
| 5,042,981 | 8/1991 | Gross | 128/852 |
| 5,234,428 | 8/1993 | Kaufman | 604/35 |
| 5,396,905 | 3/1995 | Newman | 128/853 |
| 5,524,643 | 6/1996 | Furies | 128/849 |

*Primary Examiner*—Michael A. Brown
*Attorney, Agent, or Firm*—Nawrocki, Rooney & Sivertson, P.A.

[57] ABSTRACT

An electrode carrying surgical drape and method is provided. The drape includes a polymeric film having opposing surfaces and an electrode receiving aperture therethrough. An electrode is disposed in and through the electrode receiving aperture. Electrode receiving aperture patches sealingly affix portions of said electrode to each of the opposing surfaces of the polymeric film in the vicinity of the electrode receiving aperture so as to thereby form a reinforced laminate structure capable of maintaining the sterility of an established sterile field.

8 Claims, 1 Drawing Sheet

ELECTRODE CARRYING SURGICAL DRAPE AND METHOD

TECHNICAL FIELD

The present invention relates to surgical drapes, and more particularly to an electrode carrying surgical drape which reliably maintains the sterility of an established sterile field, and further relates to a method of sealingly securing and reinforcing a traversing wire lead through sterile and non-sterile fields without compromising established sterility.

BACKGROUND OF INVENTION

The establishment and maintenance of sterile fields during surgical procedures is of the utmost importance, with swift and full recovery otherwise at risk. The sterility of a surgical procedure is only as good as its weakest link.

A great number of surgical procedures require sterile liquids to be maintained and used to lower or raise body cavity temperatures. Numerous methods and apparatuses for heating and cooling sterile surgical liquids and collecting sterile surgical slush are known in the art.

Methods of providing sterile surgical slush typically involve the scraping of congealed sterile liquid from a sterile liquid basin, more particularly from a basin conform ing surgical drape lining such a basin. As scraping methods generally jeopardize the integrity of the sterile field vis-a-vis the potential damage to the surgical drape, improved methods have focused upon indirectly breaking up the congealed liquid adhered to the drape (i.e., lifting or otherwise agitating the drape to dislodge congealed liquid). Although the risk of surgical drape leaks has been greatly reduced via indirect dislodging techniques, no means were provided to otherwise prevent damage to the surgical drape, as for instance by heating or cooling a "dry" basin, and thereby insure the integrity of the sterile field.

Techniques for preventing damage to surgical drapes and to heating and cooling mechanisms used in conjunction with apparatus for containing and thermally treating sterile liquid all require the sensing of environmental conditions external to the sterile field (e.g., temperature, conductivity, etc.). Heretofore surgical drapes have been outfitted with a variety of sensors, all having a drape plug connector (i.e., a conventional plug having socket receiving pins) positioned at a terminal end opposite the sensing element. The drape plug connectors are integral to the drapes, being attached by insertion through a grommet filled hole in the surgical drape, or by using conventional snap fasteners in combination with holders carried by the drape.

Drape plug connectors are noted to be cumbersome in the surgical room, expensive to manufacture, and subject to breaches about the grommet (i.e., more generally the interface of the plug with the drape), thereby compromising the established sterile field. Furthermore, such connectors lack the versatile required in the variety of applications confronting surgical teams.

Accordingly, it is therefore advantageous and desirable to provide a surgical drape having an unadorned wire lead traversing through sterile and non-sterile fields without comprising sterility, and an inexpensive method of producing same.

It is likewise advantageous and desirable to provide a surgical drape having a laminate structure about an electrode site that permits passage of a wire lead through sterile and non-sterile fields without comprising established sterility.

It is further beneficial and desirable to provide a surgical drape having a laminate structure about an electrode site from which portions of a drape traversing electrode extend such that connections can be made through sterile and non-sterile fields without comprising established sterility.

Similarly, it is desirous to provide a surgical drape having a reinforcingly secured wire lead traversing through sterile and non-sterile fields at an electrode site without comprising established sterility.

SUMMARY OF THE INVENTION

The present invention is directed to an electrode carrying surgical drape and method, specifically providing a drape traversing lead wire which passes therethrough and effectively "links" sterile and non-sterile fields without compromising established sterility. The electrode carrying surgical drape of the present invention includes a polymeric film having opposing surfaces and an electrode receiving aperture. An electrode is disposed in and through the electrode receiving aperture. Electrode receiving aperture patches sealingly affix portions of the electrode to each of the opposing surfaces of the polymeric film in the vicinity of the electrode receiving aperture so as to thereby form a reinforced laminate structure capable of maintaining the sterility of an established sterile field.

More specific features and advantages will become apparent with reference to the DETAILED DESCRIPTION OF THE INVENTION, appended claims, and the accompanying drawing figures.

DETAILED DESCRIPTION OF THE INVENTION

Figure 1:
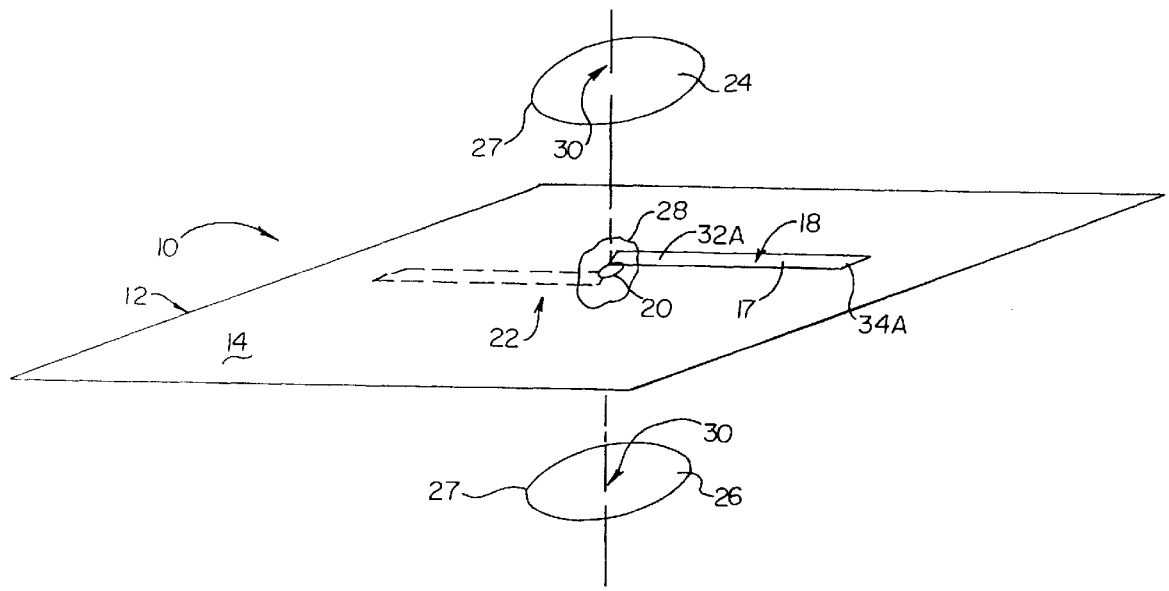
FIG. 1 is an exploded top view of the electrode carrying surgical drape of the subject invention.

With reference to the drawings, the electrode carrying surgical drape 10 generally includes a polymeric film 12 having opposing surfaces 14 & 16, an electrode 18 received in an electrode receiving aperture 20 to thereby define an electrode site 22 for the surgical drape 10, and a pair of reinforcing patches 24 & 26 affixed to each of the opposing sides 14 & 16 of the polymeric film 12, each positioned to sealingly overlay the electrode receiving aperture 20. An adhesive sealant 28 occupies any spaces or voids between the electrode 18 and the electrode receiving aperture 20, and generally coats the polymeric film 12 in the vicinity of the electrode site 22 so as to sealingly engage and adhere at least the central portion 30 of the reinforcing patches 24 & 26 to the opposing sides 14 & 16 of the polymeric film 12.

The surgical drape 10 is generally deployed so as to establish, delimit and maintain sterile and non-sterile fields, and is generally formed from a polymeric surgical drape film 12, preferably a polyurethane film having a thickness of about 0.005 inches. Alternate drape synthetics suitable to establish and maintain a sterile field are likewise contemplated, those being well known to those of skill in the art.

An integrally placed electrode 18 traverses the film 12 to thereby permit the passage of electricity, in the form of current or voltage, between the sterile and non-sterile fields without jeopardizing or compromising the sterility established by the surgical drape. Preferably the electrode 18 is a thin, dual lead, film backed conductor. In a broad sense, the electrode 18 is, in effect, a conduit linking the "environments" existing adjacent each of the opposing surfaces 14 & 16 of the polymeric film 12 when the drape 10 is deployed for use. In addition to, or beyond the passage of electricity through the established fields by the conduit, information or conditions (i.e., "data" more generally) may be passed therethrough as the application warrants, when for instance fiber optic sensors are used for a variety of detection purposes. It is to be understood that the term "electrode" used herein is not limited to electrical conductance but to conductance in its broadest sense (i.e., an electrode as a connector or linkage).

The electrode 18 is received in an aperture or passage 20 centrally positioned in the electrode site 22 so to pass through the drape film 12 (i.e., substantially intersect the plane of the drape film 12). The aperture 20 is preferable a slit (i.e., a cut with no removal of material from the drape film) dimensioned to accept the electrode 18 therethrough. Openings through the drape film may also include holes or perforations, with methods of making such openings well know to those of skill in the art of such methods.

Figure 2:
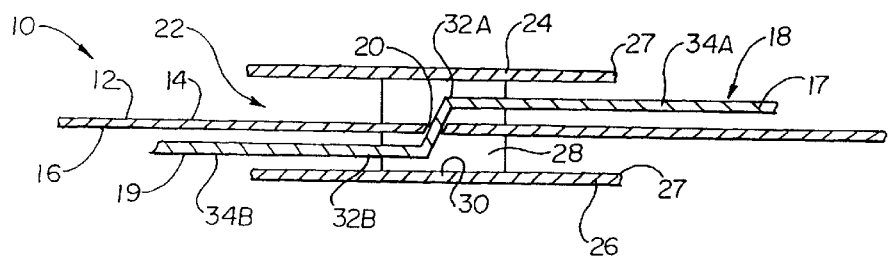
FIG. 2 is an exploded sectional view of the electrode site of the drape taken through the length the electrode.
Figure 3:
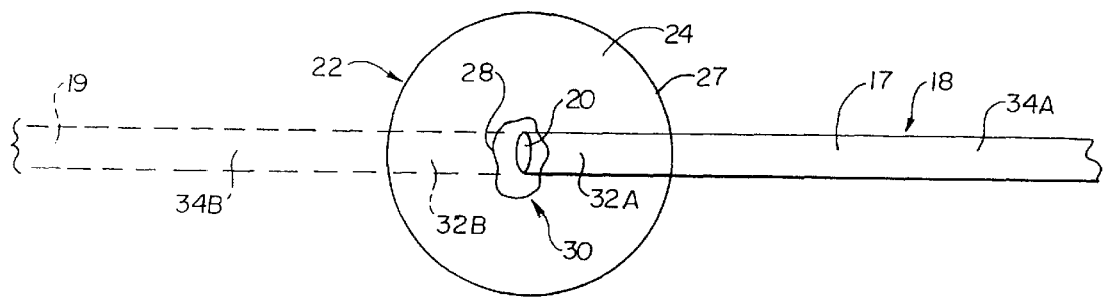
FIG. 3 is a plan view particularly illustrating the electrode site.

Referring now specifically to FIGS. 1 & 2, electrode receiving aperture patches 24 & 26 form a sealed, reinforced "sandwich" (i.e., a laminate structure) which includes several layers or partial layers, namely, a first adhesively coated polymeric patch 24, a segment 32A of a first portion 17 of the electrode 18, the polymeric film 12, a medical grade adhesive 28, a segment 32B of a second portion 19 of the electrode 18, and a second adhesively coated polymeric patch 26. This arrangement provides a strong yet simple and supremely efficient seal of the polymeric film 12 about the drape intersecting electrode 18 in the vicinity of the electrode receiving aperture or passage 20. As particularly illustrated in FIGS. 2 & 3, non-sandwiched segments 34A & 34B of the first 17 and second 19 portions of the electrode 18 extend beyond the boundary 27 of the reinforcing and sealing patches 24 & 26 so as to be suitably connected or otherwise linked to peripherals, thereby completing a transmission path between the fields.

The electrode receiving aperture patches are preferably formed from a polyethylene film or sheeting. In addition to performing a sealing function, the patches perform a reinforcement function, and as such are generally but not necessarily more rigid than the surgical drape film, and otherwise posses at least equivalent tear resistance and strength when compared to the surgical drape film.

The patches 24 & 26 are preferably centered about the electrode receiving aperture 20 on both sides of the polymeric surgical drape film 12, and preferably carry a coating of pressure sensitive adhesive on one of their surfaces so as to easily apply and affix the patch to the electrode site. Preferably the patches are circular, however other geometries are suitable. The patch is preferably dimensioned to be about 5 to 10 times the maximum dimension of the electrode aperture, however, dimensions outside this range may be more appropriate based upon factors such as aperture dimension, surgical drape material and thickness, and the physical qualities of the electrode, to name but a few parameters.

The thickness of the patches is variable, being dependent in part upon the nature of the film and patch material. Generally, sufficient sealing and reinforcement is readily achieved in the vicinity of the electrode site with patches having a thickness not greater than that of the surgical drape film itself.

In the method of forming an electrode carrying surgical drape, the polymeric surgical drape film is first slit or otherwise cut to receive an electrode. Slitting is advantageous as no material is removed from the polymeric film, thereby providing a form fit for the electrode placed therethrough. The electrode is next placed in the slit so as to form first and second electrode portions. One of the electrode portions (i.e., the first electrode portion) is partially covered by a single sided adhesive backed reinforcement patch positioned to be centered about the slit and adhered thereto. Approximately 0.1 milliliter of medical grade surgical adhesive is placed in the slit on the unpatched side of the polymeric surgical drape (i.e., in the "open" slit), and is further used to coat the segment of the second portion of the electrode to be sandwiched by the opposing patches. A second adhesive backed reinforcement patch is centered over the silicone adhesive filled slit and affixed to the surgical drape film so as to form a laminate structure.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. An electrode carrying surgical drape comprising,
   (a) a polymeric film having opposing surfaces and an electrode receiving aperture therethrough;
   (b) an electrode disposed in and through said electrode receiving aperture; and,
   (c) electrode receiving aperture patches sealingly affixing portions of said electrode to each of said opposing surfaces of said polymeric film in the vicinity of said electrode receiving aperture so as to thereby form a reinforced laminate structure capable of maintaining the sterility of an established sterile field.

2. The electrode carrying surgical drape of claim 1 wherein said electrode receiving aperture patches are substantially centered about said electrode receiving aperture.

3. The electrode carrying surgical drape of claim 1 wherein said electrode receiving aperture is a slit.

4. The electrode carrying surgical drape of claim 1 wherein said polymeric film is polyurethane.

5. The electrode carrying surgical drape of claim 1 wherein said electrode receiving aperture patches are polyethylene.

6. The electrode carrying surgical drape of claim 1 further including a layer of medical grade silicon adhesive interposed between each of said electrode receiving aperture patches and each of said opposing surfaces of said of said polymeric film.

7. A method of forming an electrode carrying surgical drape comprising the steps of:
   (a) providing a polymeric film and an electrode;
   (b) creating an electrode passage through said polymeric film;
   (c) placing said electrode through said electrode passage; and,
   (d) affixing at least a portion of said electrode relative to said polymeric film using polymeric reinforcement patches, each of said reinforcement patches being opposingly adhered about and substantially centered on said electrode passage such that the end portions of said electrode extend beyond the areal extent of each of said reinforcing patches so as to link sterile and non-sterile fields while nonetheless maintaining the sterility of said established sterile field.

8. A method of forming an electrode carrying surgical drape which reliably maintains the sterility of an established sterile field comprising the steps of:

(a) providing an electrode and a polymeric film capable of delimiting sterile and non-sterile environments;

(b) creating an electrode passage through said polymeric film;

(c) placing said electrode through said electrode passage so as to form an electrode site and define sterile and non-sterile field portions for said electrode; and, (d) reinforcingly patching said electrode site such that a first segment of said sterile field portion of said electrode is fixedly interposed between a first patch and the sterile surface of said polymeric film, and a second segment of said non-sterile field portion of said electrode is fixedly interposed between a second patch and the non-sterile surface of said polymeric film, said first and said second patches being substantially centered about said electrode passage.

* * * * *